(12) United States Patent
Kobayashi et al.

(10) Patent No.: US 8,337,552 B2
(45) Date of Patent: Dec. 25, 2012

(54) INTRAOCULAR LENS AND MANUFACTURING METHOD THEREOF

(75) Inventors: Atsushi Kobayashi, Seto (JP); Katsunori Yamada, Nagoya (JP); Hiroaki Suzuki, Tajimi (JP)

(73) Assignee: Kowa Company, Ltd., Nagoya (JP)

( * ) Notice: Subject to any disclaimer, the term of this patent is extended or adjusted under 35 U.S.C. 154(b) by 0 days.

(21) Appl. No.: 13/001,484

(22) PCT Filed: Jul. 15, 2008

(86) PCT No.: PCT/JP2008/001901
§ 371 (c)(1), (2), (4) Date: Dec. 27, 2010

(87) PCT Pub. No.: WO2010/007646
PCT Pub. Date: Jan. 21, 2010

(65) Prior Publication Data
US 2011/0098808 A1    Apr. 28, 2011

(51) Int. Cl.
*A61F 2/16* (2006.01)
(52) U.S. Cl. ........................................... 623/6.11
(58) Field of Classification Search ............. 623/4.1, 623/6.11, 6.56, 6.62, 5.15, 5.16
See application file for complete search history.

(56) References Cited

U.S. PATENT DOCUMENTS

| 4,449,257 A | 5/1984 | Koeniger |
| 5,405,385 A | 4/1995 | Heimke et al. |
| 6,140,438 A | 10/2000 | Ojio et al. |
| 2006/0122700 A1 | 6/2006 | Kurosaka et al. |

FOREIGN PATENT DOCUMENTS

| JP | A-10-24097 | 1/1998 |
| JP | A-11-56998 | 3/1999 |
| JP | A-11-505453 | 5/1999 |
| JP | A-2005-507742 | 3/2005 |
| WO | WO 03/039409 A1 | 5/2003 |
| WO | WO 2004/096099 A1 | 11/2004 |

OTHER PUBLICATIONS

International Search Report issued in International Application No. PCT/JP2008/001901 on Aug. 12, 2008 (with translation).

*Primary Examiner* — William H. Matthews
(74) *Attorney, Agent, or Firm* — Oliff & Berridge

(57) ABSTRACT

An intraocular lens adapted for deployment within a lens capsule. At least part of a lens surface of the intraocular lens constitutes a cell inducing region in which are directly formed a multitude of microgrooves. The microgrooves take a form of minute linear grooves and lands of depth dimension between 0.01 and 1.0 μm and width dimension between 0.1 and 2.0 μm extending with prescribed length in a circumferential direction on the lens surface. The minute linear grooves and lands are formed with a chained pattern connected in the circumferential direction of the lens surface and with a periodic pattern arrayed periodically in a diametrical direction so that the minute linear grooves and lands are formed without intervening spaces throughout the entire cell inducing region and impart visible light transmittance of 60% or above to the cell inducing region.

12 Claims, 7 Drawing Sheets

LENS CIRCUMFERENTIAL DIRECTION

LENS CIRCUMFERENTIAL DIRECTION

LENS CIRCUMFERENTIAL DIRECTION

INTRAOCULAR LENS AND MANUFACTURING METHOD THEREOF

TECHNICAL FIELD

The present invention relates to an intraocular lens adapted for use while accommodated within the lens capsule, and relates in particular to an intraocular lens that is effective in inhibiting secondary cataracts.

BACKGROUND ART

Intraocular lenses intended to replace the crystalline lens have been used for some time to treat patients suffering from ocular disorders such as cataracts. In a typical procedure, after extracting and removing the crystalline lens from inside the capsule through a surgical incision made in the ocular tissue, such as the cornea (sclera) or anterior capsule portion of the lens, an insertion instrument or the like is used to insert the intraocular lens into the capsule through the surgical incision while folded back onto itself. Once inserted into the capsule, the intraocular lens is deployed inside the capsule to allow it to be used with the optical part thereof, which replaces the functionality of the crystalline lens, securely positioned within the capsules by means of support portions.

Secondary cataracts are a subsequent complication sometimes encountered as a problem with intraocular lens replacements. Secondary cataracts occur when subsequent to surgery, the epithelial cells of the crystalline lens grow around to the back face of the intraocular lens, clouding the posterior capsule to the back side of the intraocular lens and causing a decline in vision.

One known technique for inhibiting secondary cataracts, disclosed for example in Patent Document 1 and Patent Document 2, involves imparting sharp edge contours to the outside peripheral edge portion of the back face of the optical part of the intraocular lens, and deploying the lens within the capsule so that the sharp edge presses against the posterior capsule, thereby preventing epithelial cells of the crystalline lens from growing around towards the lens back face. However, with this method the optical part tends to be thicker as a result of the sharp edge contours, and the surgical incision required for insertion into the capsule must be larger, posing the problem of difficulty in folding the lens during the insertion process.

In Patent Document 3 there is proposed an intraocular lens having at least one annular groove extending continuously in the circumferential direction through the outside peripheral section of the intraocular lens and formed with a cross section sufficiently large to accommodate epithelial cells on the crystalline lens, and provided on the surface of this annular groove with a microgrooved irregular face. According to this intraocular lens, through a feature combining this large annular groove with a microgrooved irregular face, epithelial cells on the crystalline lens may be captured in the annular groove in the outside peripheral section of the intraocular lens, preventing growth of epithelial cells on the crystalline lens towards the center section of the intraocular lens.

However, in order for the feature of combining a large annular groove and a microgrooved irregular face as taught in Patent Document 3 to afford effective action in trapping epithelial cells on the crystalline lens and inhibiting epithelial cell growth, the annular groove must be formed with a size enough to create an opaque section in which light is not able to be focused on the retina. Thus, the intraocular lens disclosed in Patent Document 3 has, in the outside peripheral section thereof where the annular groove is formed, an opaque section that cannot be employed as part of the effective optical part. The effective optical part of an intraocular lens is preferably as large as possible so as to ensure that sufficient light enters under conditions of limited outside diameter dimension imposed by deploying of the lens within the lens capsule, and to provide a good field of vision through overlap of the entire pupil in a reliable manner. However, because the outside peripheral section of the intraocular lens taught in Patent Document 3 is an opaque section, an adequate effective optical part is not necessarily assured, making it difficult to provide a good field of vision.

Patent Document 1: JP-A 2005-507742
Patent Document 2: WO 2004/096099
Patent Document 3: JP-A 11-505453

DISCLOSURE OF THE INVENTION

Problem the Invention Attempts to Solve

With the foregoing in view, it is accordingly an object of the present invention to provide an intraocular lens of novel design whereby sufficiently large size of the effective optical part is assured, while also affording excellent ability to inhibit the development of secondary cataracts.

It is a further object of the invention to provide a novel manufacturing method for an intraocular lens whereby such an intraocular lens may be manufactured advantageously.

Means for Solving the Problem

The above objects may be attained according to the following modes of the invention. The elements employed in each of the following modes of the invention may be adopted at any possible optional combinations. It is to be understood that the modes and technical features of the invention are not limited to those disclosed herein, but are recognized based on the entire specification and drawings, or on the basis of inventive concepts that would be apparent to those skilled in the art in the light of the present disclosure.

Specifically, a first mode of the present invention relating to an intraocular lens provides an intraocular lens adapted for deployment within a lens capsule, being characterized in that: at least part of a lens surface constitutes a cell inducing region in which are directly formed a multitude of microgrooves; the microgrooves take a form of minute linear grooves and lands of depth dimension between 0.01 and 1.0 μm and width dimension between 0.1 and 2.0 μm extending with prescribed length in a circumferential direction on the lens surface; and the minute linear grooves and lands are formed with a chained pattern connected in the circumferential direction of the lens surface and with a periodic pattern arrayed periodically in a direction orthogonal to the circumferential direction of the lens surface so that the minute linear grooves and lands are formed without intervening spaces throughout the entire cell inducing region and impart visible light transmittance of 60% or above to the cell inducing region.

In the intraocular lens constructed according to the present mode, the minute linear grooves and lands that are formed in the cell inducing region and extend in the lens circumferential direction function to align (induce) the direction of growth of crystalline lens epithelial cells (thought to be the cause of secondary cataracts) with the lens circumferential direction in which the minute linear grooves and lands extend. When cells growing along the minute linear grooves and lands reach confluence, further growth stops due to contact inhibition. Accordingly, growth of cells towards the lens center section is checked, thus providing excellent suppression of secondary cataracts.

Moreover, according to the present mode, the lens can be thinner because there is no need to form a sharp edge contour. Accordingly, the lens is easily folded over during insertion into the lens capsule, facilitating the insertion procedure and reducing the burden on the patient as well. However, the invention is not intended to exclude adoption of a sharp edge contour, and it is possible for the invention to be combined with a sharp edge contour.

According to the present mode in particular, by directly forming on the lens surface minute linear grooves and lands of size equal to the specific dimensions taught above, visible light transmittance of 60% or above may be assured in the cell inducing region in which the minute linear grooves and lands are formed. Herein, visible light transmittance refers to transmittance of visible light of wavelengths of about 350 nm to about 800 nm. The crystalline lens epithelial cells thought to cause secondary cataracts have been found to have hexagonal rod shape with diameter of about 13 to 22 μm and height of 25 μm; the dimensions of the minute linear grooves and lands in the present mode are smaller than these crystalline lens epithelial cells, and are such that no adverse tactile or visual effects arise during wear, making them imperceptible to the wearer.

According to the present mode, the microgrooves are formed directly on the lens surface. Herein, the term lens surface is used to include the lens front face positioned towards the cornea side when deployed in the lens capsule, the lens back face positioned towards the posterior capsule when deployed in the lens capsule, and the surface of the edge portion in which the lens front face connects with the lens back face. For example, in consideration of the pathogenesis of secondary cataracts, microgrooves may be formed on the lens surface on the lens back side only. Direct formation of microgrooves on the lens surface does not refer to formation of an annular groove larger in size than cells that cause secondary cataracts, followed by formation of microgrooves on the bottom and side faces of this annular groove; but rather refers to lens surface contours defined by a predetermined base contour face, e.g. a spherical convex face, spherical concave face, or flat face, that is smooth overall and on whose base contour face the microgrooves have been formed directly. Specifically, the lens surface having an intraocular lens base contour designed on the basis of the required optical properties is not furnished with an irregular contour like the annular groove taught in Patent Document 3. Rather, microgrooves are formed on a lens surface having this base contour. Accordingly, the lens surface in the present mode has a very low level of surface roughness associated with direct formation of microgrooves having the specific dimensions taught herein, so the lens surface does not take on the appearance of frosted glass, and there is negligible risk of diminished transparency. Additionally, where the microgrooves meet prescribed conditions such as the refractive index of the contacting medium, iridescence caused by splitting of light may be observed, but because this splitting of light is reduced by the aqueous humor, glare is minimized. As a result, a sufficient level of transmittance of visible light may be assured in the cell inducing region where the microgrooves are formed, and sufficiently large size of the effective optical part may assured, while affording excellent ability to inhibit the development of secondary cataracts.

The chained pattern of minute linear grooves and lands connected in the circumferential direction of the lens surface that is taught in the present mode refers to one in which the minute linear grooves and lands, viewed in the lens circumferential direction, are formed so as to conjoin with their ends connected to one another with substantially no space between them in the circumferential direction. In preferred practice, a multitude of minute linear grooves and lands are formed respectively extending for prescribed length in the circumferential direction and arrayed generally parallel to one another in the direction orthogonal to the circumferential direction of the lens surface, with the multitude of minute linear grooves and lands arrayed in the direction orthogonal to the circumferential direction of the lens surface being formed such that their circumferential ends do not line up with one another at the same location in the lens circumferential direction. In other words, where a line is extended in the direction orthogonal to the circumferential direction of the lens surface through circumferentially connected regions of minute linear grooves and lands in the lens direction, the other minute linear grooves and lands extend continuously through this line in the circumferential direction. Thus, at least one linear microgroove is present at any location in the direction orthogonal to the circumferential direction of the lens surface about the entire circumference in the circumferential direction of the lens surface, thereby preventing the circumferential connecting regions of the multitude of minute linear grooves and lands arrayed in the direction orthogonal to the circumferential direction of the lens surface from linking up to produce a substantially grooved portion extending in the lens diametrical direction. The direction orthogonal to the circumferential direction of the lens surface refers, in the case that the lens surface is the lens front face or the lens back face, to the lens diametrical direction, or where the lens surface is the surface of the edge portion (lens outside peripheral edge face), to the lens thickness direction. Formation of minute linear grooves and lands with no spaces refers to forming minute linear grooves and lands situated adjacently in the lens circumferential direction or the direction orthogonal to the circumferential direction, in such a way that they connect with one another and such that the base contour face of the lens surface is not apparent between these adjacent minute linear grooves and lands.

As mentioned previously, in the present mode, direct formation of microgrooves on the lens surface refers not to a process of direct formation on the lens surface, although the microgrooves indeed may be formed on the lens surface through such a direct process. However, as will be described later, it is preferable for the microgrooves to be formed on a resin mold used to mold the lens, on the die used to produce the resin mold, or on the die used for direct molding of the lens, and transferred to the lens. Better manufacturing efficiency is afforded thereby.

A second mode of the present invention relating to an intraocular lens provides an intraocular lens according to the first mode wherein the minute linear grooves and lands have circumferential length dimensions of between 1.0 and 50.0 μm.

According to the present mode, the growth direction of cells causing secondary cataracts may be oriented in the lens circumferential direction so as to effectively limit their growth towards the lens center section, as well as making the minute linear grooves and lands easy to form. However, if the circumferential length dimensions of the minute linear grooves and lands are smaller than 1.0 μm, their effect of orienting the direction of cell growth is not adequate, whereas if the length exceeds 50.0 μm, substantially no difference in effect of orienting the direction of cell growth is achieved, and linear microgroove sizes in excess of 50.0 μm also make volume production difficult.

A third mode of the present invention relating to an intraocular lens provides an intraocular lens according to the first or second mode, wherein the cell inducing region is formed in an outside peripheral section of at least one of a lens front face and a lens back face. According to the present mode, the cell inducing region is endowed with appropriate width dimensions in the lens diametrical direction, so as to enable formation of a multitude of minute linear grooves and lands in the lens diametrical direction. Thus, in the unlikely event that cells causing secondary cataracts should begin to grow out from a specific linear microgroove and towards the inward side in the lens diametrical direction, the additional minute linear grooves and lands formed further towards the inward side thereof in the lens diametrical direction may act to more effectively redirect the growth direction towards the lens circumferential direction, so that growth of these cells towards the lens center section may be inhibited more effectively.

A fourth mode of the present invention relating to an intraocular lens provides an intraocular lens according to the third mode, wherein the cell inducing region is formed on at least one of the lens front face and the lens back face, exclusively in the outside peripheral section thereof which excludes a center section. According to the present mode, it is possible to effectively avoid the risk of adverse effects on vision caused by the minute linear grooves and lands formed in the cell inducing region. Specifically, according to a fifth mode of the present invention relating to an intraocular lens according to the fourth mode, the cell inducing region that is formed exclusively in the outside peripheral section of at least one of the lens front face and the lens back face is a region extending 2 mm or less in a lens diametrical direction from a lens outside edge.

A sixth mode of the present invention relating to an intraocular lens provides an intraocular lens according to any of the first to fifth modes, wherein the minute linear grooves and lands are formed on a surface of an edge portion which includes a lens outside edge face, and the cell inducing region includes the surface of the edge portion. According to the present mode, the effect of inducing the direction of growth of cells that cause secondary cataracts may be attained in the edge portion as well.

A seventh mode of the present invention relating to an intraocular lens provides an intraocular lens according to any of the first to sixth modes, wherein in a cross section of the cell inducing region taken in a direction orthogonal to a lens circumferential direction, the minute linear grooves and lands are formed with periodic cross sectional contours represented by a periodic function.

According to the present mode, large deviations in width dimension among minute linear grooves and lands may be avoided, and all of the minute linear grooves and lands may be imparted with generally equal ability to induce the growth direction of cells that cause secondary cataracts. More specifically, the periodic cross sectional contour according to the present mode refers to a continuous periodic pattern of cross sectional contours represented by a sinusoidal curve or a polynomial function curve.

An eighth mode of the present invention relating to an intraocular lens provides an intraocular lens according to any of the first to seventh modes, wherein at least one of the lens surfaces is formed using a resin mold molded by a die having minute linear grooves and lands formed on a molding face thereof so that the minute linear grooves and lands are transferred therefrom; and the cell inducing region is formed through transfer of the minute linear grooves and lands on the resin mold to the lens surface.

According to the present mode, minute linear grooves and lands formed on a resin mold are transferred to the lens surface, thus affording excellent manufacturing efficiency, as well as enabling production of the minute linear grooves and lands on lenses in a consistently reproducible manner. Additionally, the present mode merely entails forming minute linear grooves and lands on the die, while subsequent steps may be carried out comparably to conventional in-mold casting processes, so there is substantially no increase in the number of steps on the lens production line, and minute linear grooves and lands can be produced in a manner that is efficient and consistently reproducible. Additionally, because it suffices to use a die with minute linear grooves and lands formed thereon as the die for molding the resin mold, conventional resin mold molding units and in-mold casting production equipment used to cast lenses may be utilized without modification for the purpose of forming minute linear grooves and lands onto the lens surface. Also, because the minute linear grooves and lands formed on the die are transferred to each lens through the agency of the resin mold, it is possible to minimize deviation in contours among minute linear grooves and lands formed on the lenses.

A first aspect of the present invention relating to an intraocular lens manufacturing method provides a method of manufacturing an intraocular lens adapted for deployment within a lens capsule comprising the steps of: forming at least one of lens surfaces using a resin mold molded by a die; subjecting a resin mold molding face of the die to bombardment with at least one of radiation and a laser beam to produce microgrooves thereon; transfer molding the microgrooves produced on the die to a lens molding face of the resin mold; and retransferring the microgrooves that were transferred to the resin mold at least one of the lens surfaces to form on at least a portion of the lens surface a cell inducing region having a multitude of microgrooves directly formed therein, wherein the microgrooves take the form of minute linear grooves and lands of depth dimension between 0.01 and 1.0 μm and width dimension between 0.1 and 2.0 μm extending with prescribed length in a circumferential direction on the lens surface, and the minute linear grooves and lands are formed with a chained pattern connected in the circumferential direction of the lens surface and with a periodic pattern arrayed periodically in a direction orthogonal to the circumferential direction of the lens surface so as to form the minute linear grooves and lands without intervening spaces throughout the entire cell inducing region and impart visible light transmittance of 60% or above to the cell inducing region.

The present mode affords advantageous manufacture of an intraocular lens assured to have an effective optical part of sufficiently large size, while affording excellent ability to inhibit the development of secondary cataracts. Specifically, minute linear grooves and lands formed on a die are transferred to a resin mold, and the lens surface is then molded with the resin mold, so the only additional step involved is one to produce the minute linear grooves and lands on the die, whereas the subsequent steps for forming resin molds using dies and for in-mold casting of the lens using resin molds may take place in the same manner as conventional process steps, to obtain the intraocular lens having minute linear grooves and lands. Consequently there is substantially no increase in steps on the production line, and the minute linear grooves and lands can be produced in a highly reproducible manner with excellent manufacturing efficiency, while minimizing deviation in contours among minute linear grooves and lands formed on the lenses.

According to the present mode in particular, because the microgrooves are formed on the resin molding face of the die by subjecting it to bombardment with at least one of radiation and a laser beam, microgrooves may be formed with better reproducibility and greater precision as compared with a cutting process or the like. In preferred practice, radiation or a laser beam is used in such a way that the machining face is machined without becoming hot. By so doing thermal deformation of the machining face may be minimized, and the microgrooves may be produced with greater precision. No limitations are imposed as to type of radiation employed provided that the machining face is able to be machined; examples include electron beams, particle beams, x rays, γ rays, and the like.

A second mode of the invention relating to an intraocular lens manufacturing method provides a method of manufacturing an intraocular lens according to the first mode, wherein the laser beam is a laser beam having a pulse width of between $1 \times 10^{-16}$ second and $1 \times 10^{-7}$ second.

According to the manufacturing method of the present mode, the minute linear grooves and lands may be formed advantageously. The reason is that generating a laser beam of pulse widths shorter than $1 \times 10^{-16}$ second requires highly accurate oscillation control, whereas pulse widths longer than $1 \times 10^{-7}$ second are not able to produce distinct minute linear grooves and lands. More preferably, a laser beam having a pulse width of between $1 \times 10^{-15}$ second and $1 \times 10^{-9}$ second is used. This allows conventional known general-purpose laser machining equipment to be used, thus contributing to lower manufacturing costs and affording efficient production of the minute linear grooves and lands. In preferred practice, bombardment will take place at output close to the ablation threshold of the laser. This makes it possible to provide more consistent formation of periodic continuous minute linear grooves and lands in the lens diametrical direction.

The scientific grounds as to why the use of a laser beam having a pulse width of between $1 \times 10^{-16}$ second and $1 \times 10^{-7}$ second is advantageous for producing the minute linear grooves and lands is poorly understood, nor is it an object of the invention to shed light upon such scientific grounds; however, when a laser beam of pulse width between $1 \times 10^{-16}$ second and $1 \times 10^{-7}$ second directed onto a machining face is scattered at the surface of the machining face, surface scattered light is produced. Through ablation arising in sections of interference of this surface scattered light with the impinging laser beam, surface roughness is increased in the interference sections. The intensity of surface scattered light during subsequent laser bombardment is boosted thereby, and ablation advances further, while interference arises at a location one wavelength away as well. It is surmised that minute linear grooves and lands are formed advantageously through more effective ablation brought about by repeated shots of a laser beam of pulse width between $1 \times 10^{-16}$ second and $1 \times 10^{-7}$ second in this way, while also minimizing heat-induced deformation, to afford better machining precision.

KEYS TO SYMBOLS

Figure 1:
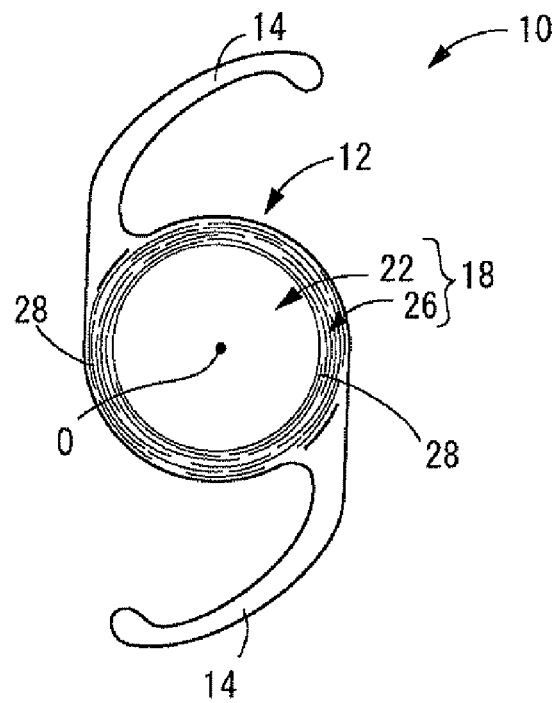
FIG. 1 is a rear view of an intraocular lens according to an embodiment of the present invention.

10 Intraocular lens
12 Optical part
14 Haptic
16 Lens front face
18 Lens back face
20 Front face center portion
22 Back face center portion
24 Front face peripheral portion
26 Back face peripheral portion
28 Microgrooves
30 Edge portion
32 Outside peripheral face

BEST MODE FOR CARRYING OUT THE INVENTION

A fuller understanding of the present invention is provided by the following detailed description of the preferred embodiments with reference to the accompanying drawings.

First, FIG. 1 depicts an intraocular lens 10 according to an embodiment of the present invention. The intraocular lens 10 structure includes an optical part 12 designed to have optical properties substituting for those of the crystalline lens of the human eye, and a pair of haptics 14 adapted to support the optical part 12 inside the lens capsule. FIG. 1 depicts a lens back view; in FIG. 1 and in FIG. 2 to be discussed later, the microgrooves 28 (described later) are depicted with exaggerated size.

Turning to a more detailed description, the optical part 12 is generally disk shaped and appears circular in front view, and has a lens front face 16 which is positioned towards the cornea and a lens back face 18 which is positioned towards the posterior capsule, with the lens arranged inside the lens capsule. The lens front face 16 and the lens back face 18 may be given various contours according to the optical properties required, and any combination of concave face, convex face, flat face etc. may be selected for the contours of the two faces 16, 18. The present embodiment employs a convex lens shape in which both the lens front face 16 and the lens back face 18 are outwardly convex spherical convex faces, and the optical axis: O of the optical part 12 is aligned with the geometric axis of the optical part 12.

The pair of haptics 14 extend respectively outward from the optical part 12 at two locations on the outside peripheral edge part of the optical part 12 at locations of 180 degree rotational symmetry to one another about the geometric axis of the optical part 12, and then curve to follow the contour of the optical part 12 in the circumferential direction.

While the present invention may also be implemented in a two piece intraocular lens or a three piece intraocular lens in which the optical part 12 and the haptics 14 are formed separately, in the present embodiment in particular, the intraocular lens 10 is a one piece intraocular lens in which the optical part 12 and the pair of haptics 14 are integrally formed, preferably by the manufacturing method described later.

The material of which the intraocular lens 10 is formed may be selected from various materials having ample visible light transmittance for use as an intraocular lens, as well as excellent flexibility and a certain degree of elasticity. Flexible materials having a glass transition point of no more than 30° C. and refractive index of at least 1.51 are preferred. Such flexible materials allow the intraocular lens 10 to be easily folded over on itself or rolled up at normal temperature to make it even more compact, thus providing greater ease of insertion into the capsule during implantation.

Specifically, the materials disclosed in JP-A 10-24097 and JP-A 11-56998 are favorable for use as materials forming the intraocular lens 10 of the present invention. Among these, monomers including one or more (meth)acrylic acid esters like those listed in (i) below are especially preferred as they afford an intraocular lens with exceptional shape recovery. The optional monomers listed in (ii) below may be included as well. Optionally, adjuvants such as those listed in (iii) below may be added as needed.

(i) Included Monomers

Linear, branched, or cyclic alkyl (meth)acrylates such as the following:

methyl(meth)acrylate, ethyl(meth)acrylate, butyl(meth)acrylate, cyclohexyl(meth)acrylate, etc.

Hydroxyl-containing (meth)acrylates such as the following:

hydroxyethyl(meth)acrylate, hydroxybutyl(meth)acrylate, diethylene glycol mono(meth)acrylate, etc.

Aromatic ring-containing (meth)acrylates such as the following:

phenoxyethyl(meth)acrylate, phenyl(meth)acrylate, phenylethyl(meth)acrylate, etc.

Silicon-containing (meth)acrylates such as the following:

trimethylsiloxy dimethyl silyl methyl(meth)acrylate, trimethylsiloxy dimethyl silyl propyl(meth)acrylate, etc.

Herein, "(meth)acrylate" is used as the common designation for the two compounds "acrylate" and "methacrylate"; this convention is employed for the other (meth)acrylic acid derivatives described later as well.

(ii) Optional Monomers (Meth)acrylamide and derivatives thereof such as the following:

(meth)acrylamide, N,N-dimethyl(meth)acrylamide, etc.

N-vinyl lactams such as the following:

N-vinylpyrrolidone etc.

Styrene and derivatives thereof

Crosslinking monomers such as the following:

butanediol di(meth)acrylate, ethylene glycol di(meth)acrylate (iii) Adjuvants

Thermal polymerization initiators, photopolymerization initiators, photosensitizers, etc.

Dyes, etc.

UV absorbers, etc.

In the present embodiment in particular, the lens front and back faces 16, 18 respectively include front/back face center portions 20, 22 in their center section, and front/back face peripheral portions 24, 26 that encircle the front/back face center portions 20, 22 about the entire circumference. The front/back face peripheral portions 24, 26 respectively have annular shape centered on the geometric axis of the optical part 12 and extending continuously around in the circumferential direction with prescribed diametrical width dimension, with the front/back face peripheral portions 24, 26 connecting at their inside peripheral edge section to the front/back face center portions 20, 22 respectively. In the present embodiment, the front face center portion 20 and front face peripheral portion 24 that make up the lens front face 16 connect smoothly with a common tangent, and the front face peripheral portion 24 has a base contour face defined by a smooth spherical convex face continuing out from the front face center portion 20.

Figure 3:
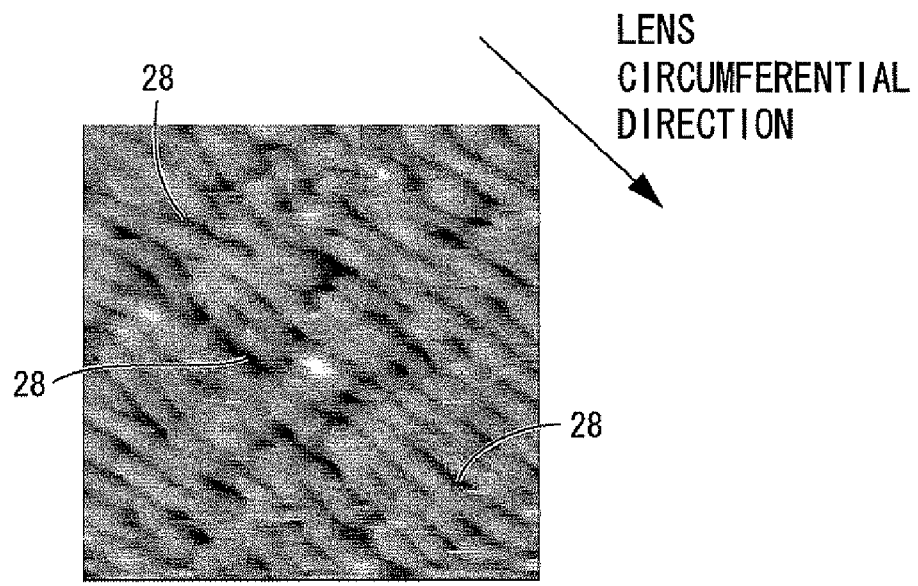
FIG. 3 shows an observed image of surface contours of a cell inducing region of the intraocular lens of FIG. 1.
Figure 4:
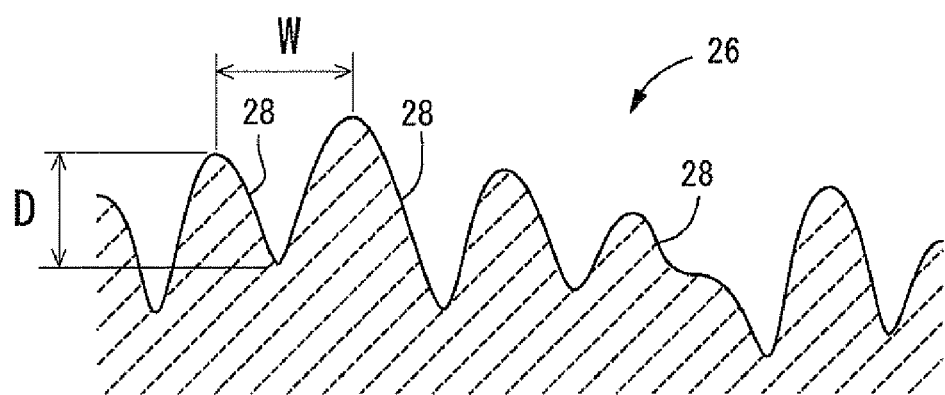
FIG. 4 is a specific view depicting cross sectional contours of the cell inducing region of FIG. 3.

Meanwhile, the back face peripheral portion 26 constitutes a cell inducing region extending with prescribed length dimension in the lens circumferential direction and containing a multitude of microgrooves 28 formed therein without spaces. FIG. 3 depicts the surface of the back face peripheral portion 26 in model form; and FIG. 4 is cross section of the back face peripheral portion 26 taken in the lens diametrical direction, and depicts in model form a cross section in the direction of periodicity of a periodic pattern that is formed by the microgrooves 28. The arrow in FIG. 3 indicates the lens circumferential direction. Preferably, the back face peripheral portion 26 is formed with annular shape in a region extending no more than 2 mm in the lens diametrical direction from the outside peripheral edge of the optical part 12, while the zone lying within 3 mm of the optical part center in the lens diametrical direction constitutes the front face center portion 20 devoid of microgrooves 28.

The microgrooves 28 are recessed slots that open outwardly onto the lens and have size smaller than cells that cause secondary cataracts. Specifically, it is preferable for depth dimension D: thereof to be selected within the range $0.01\ \mu m \leq D \leq 1.0\ \mu m$, and the width dimension W: to be selected within the range $0.1 \leq W \leq 2.0\ \mu m$. The microgrooves 28 may take continuous annular shape extending about the entire lens circumference, or be formed with circumferential length dimensions such that they are not continuous about the entire lens circumference, but instead are branched at some point along the way. In preferred practice, circumferential length dimensions of the microgrooves 28 will be selected within a range between 1.0 μm and 50.0 μm. From FIG. 3 it will be appreciated that according to the present embodiment, the microgrooves 28 extending in the lens circumferential direction do not always extend in precise alignment with the lens circumferential direction, but rather extend with a lens direction component which is accompanied by varying degrees of skew.

The multitude of microgrooves 28 are formed directly on the surface of the back face peripheral portion 26, with appropriate spacing in the lens diametrical direction. The microgrooves 28 thereby form groove portions that extend for prescribed length in the circumferential direction on the lens surface and that define between these microgrooves 28 land portions extending for prescribed length in the circumferential direction on the lens surface. Thus, on the surface of the back face peripheral portion 26, these groove portions and land portions give rise to minute linear grooves and lands having a periodic groove/land pattern in the lens diametrical direction, formed directly on the base contour face of the spherical convex lens back face 18.

As depicted in model form in FIG. 1, about the entire circumference along the circumferential direction of the back face peripheral portion 26, at least one microgroove 28 is formed at any location in the lens diametrical direction; in other words, along the entire circumference, at least one microgroove 28 is formed on the back face peripheral portion 26. The minute linear grooves and lands are thereby connected in a chained pattern in the circumferential direction of the back face peripheral portion 26.

At the same time, the plurality of microgrooves 28 have a periodic arrangement in the lens diametrical direction such that the minute linear grooves and lands formed by these microgrooves 28 and the land portions between them are periodically arranged in a periodic pattern in the lens diametrical direction; as depicted in model form in FIG. 4, their cross sectional contours taken in the lens diametrical direction are sinusoidal curving contours.

Thus, on the surface of the back face peripheral portion 26, the groove portions defined by the microgrooves 28 and the land portions situated between them are formed in alternating fashion in the lens circumferential direction and the lens diametrical direction; groove portions and land portions adjacently situated in the lens circumferential direction and/or the lens diametrical direction are formed connecting with one another; and the base contour face of the lens back face 18 is not apparent between these adjacent groove portions and land portions. As a result, the minute linear grooves and lands are formed with no spaces, over the entire surface of the back face peripheral portion 26.

Here, because the microgrooves 28 are extremely small in size, visible light transmittance of at least 60% is assured in the back face peripheral portion 26 where the microgrooves 28 are formed.

Figure 2:
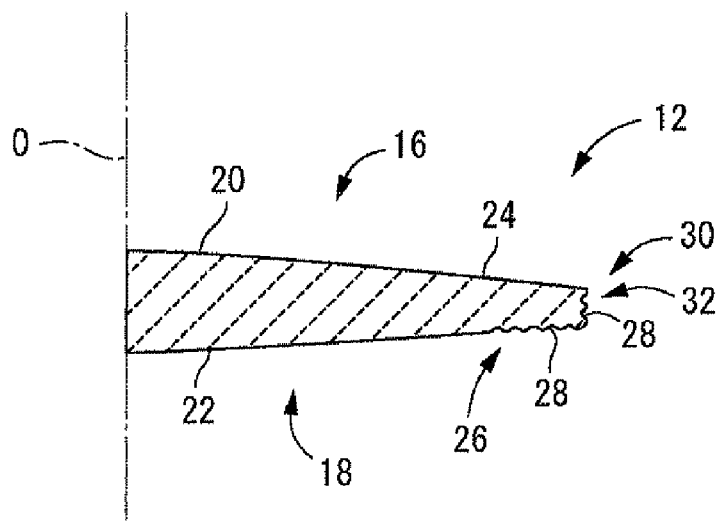
FIG. 2 is a cross sectional specific view suitable for explaining an optical part of the intraocular lens of FIG. 1.

As depicted in model form in FIG. 2, in the present embodiment in particular, the outside peripheral face 32 of the edge portion 30 connecting the lens front face 16 and the lens back face 18 is also constituted as a cell inducing region having microgrooves 28 formed thereon. The microgrooves 28 that are formed on the outside peripheral face 32 of the edge portion 30 are comparable in structure to the microgrooves 28 formed on the back face peripheral portion 26 and will not be discussed in any detail, except to note that the microgrooves 28 formed in the edge portion 30 are constituted as grooves formed directly on the outside peripheral face 32 of the edge portion 30 and that open outward in the lens diametrical direction while extending with prescribed dimension in the lens circumferential direction. These microgrooves 28 are formed with periodicity in the lens thickness direction (the vertical direction in FIG. 2) such that, viewed in cross section of the edge portion 30 taken in the lens thickness direction, the minute linear grooves and lands defined by the microgrooves 28 and land portions therebetween have sinusoidal curving contours. Thus, the minute linear grooves and lands defined by the microgrooves 28 and land portions therebetween are formed without intervening spaces, over the entire outside peripheral face 32 of the edge portion 30.

In this way, the intraocular lens 10 according to the present embodiment has microgrooves 28 formed over the entire back face peripheral portion 26 which constitutes the outside peripheral section of the lens back face 18 and over the entire outside peripheral face 32 of the edge portion 30, so that the back face peripheral portion 26 and the outside peripheral face 32 of the edge portion 30 serve as cell inducing regions.

Using an appropriate insertion instrument if needed, the intraocular lens 10 having the above construction is folded over onto itself, and in this condition is inserted into the lens capsule through an incision made in the capsule. Once inserted into the capsule, the intraocular lens 10 expands so as to return to its initial state through intrinsic elastic force, and with the optical part 12 being positioned supported at a prescribed location inside the capsule by the pair of haptics 14 is deployed within the capsule with the lens back face 18 disposed in contact against the posterior capsule.

In the intraocular lens 10 constructed in accordance with the present embodiment, the microgrooves 28 and intervening land portions formed in the back face peripheral portion 26 create minute linear grooves and lands that extend in the lens circumferential direction through the entire back face peripheral portion 26. Thus, the direction of growth of cells that cause secondary cataracts by growing over the surface of the back face peripheral portion 26, in other words, over the posterior capsule, may be directed towards the direction of extension of the microgrooves 28, that is, in the lens circumferential direction. Additionally, when the cells reach confluence, their growth stops due to contact inhibition. As a result, cell growth towards the lens center section may be checked, thus providing excellent suppression of secondary cataracts. Further, in the present embodiment in particular, by forming minute linear grooves and lands on the outside peripheral face 32 of the edge portion 30 as well, the cell growth direction can be directed towards the lens circumferential direction by the edge portion 30 as well, making it possible to more effectively inhibit cell growth towards the lens center section.

Moreover, in the present embodiment in particular, because the minute linear grooves and lands are formed directly on the lens surface, it is possible to avoid a frosted glass appearance of the lens surface, and visible light transmittance of at least 60% is assured. Thus, the back face peripheral portion 26 can also be utilized as part of the effective optical part, and the effective optical part of the intraocular lens may be assured to have the largest possible diameter despite appreciable limitations as to lens diameter dimension imposed by deployment within the capsule, while at the same time affording exceptional ability to inhibit the development of secondary cataracts. Moreover, in the present embodiment, on the lens front and back faces 16, 18 which have an effect on the optical properties, only the back face peripheral portion 26 constitutes the cell inducing region in which the microgrooves 28 are formed, while the entirety of the lens front face 16 and the back face center portion 22 are devoid of microgrooves 28, thereby further reducing possible effects on the optical properties.

The description turns next to a specific example of an advantageous manufacturing method for the intraocular lens 10 constructed as discussed above.

Figure 5A:
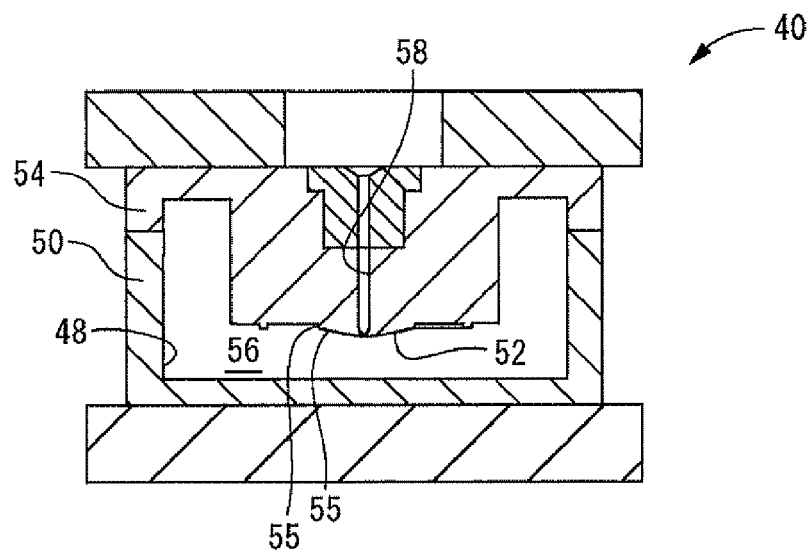
FIGS. 5A and 5B are longitudinal sectional specific views depicting a die for use in production of the intraocular lens shown in FIG. 1.
Figure 5B:
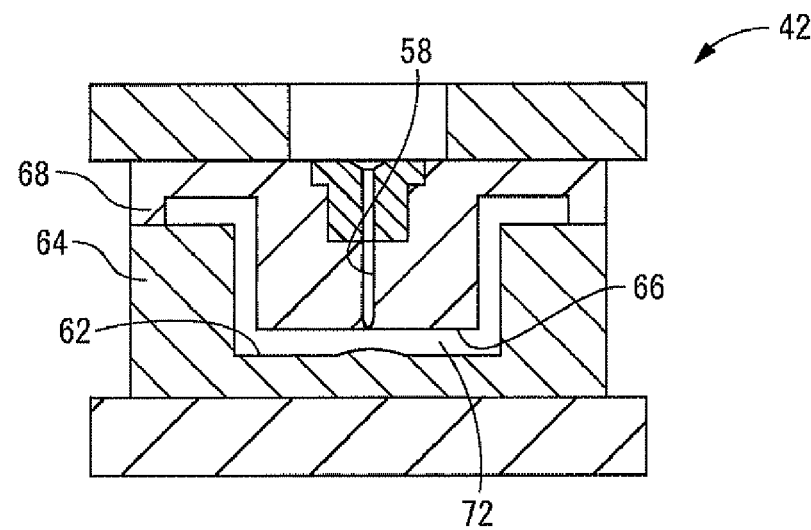

First, as shown in FIGS. 5A and 5B, the dies, namely a female mold molding die 40 and a male mold molding die 42, are prepared. The female and male mold molding dies are used in a known resin molding process for independently manufacturing a lens casting female die 44 (see FIG. 6) and a lens casting male die 46 (see FIG. 6) to be employed as resin molds for producing the objective intraocular lens 10 through in-mold casting (polymerization). In particular, the molding dies are preferably made of pre-hardened steel or other material suited to laser machining, discussed later, but other metal materials may be used. Thermoplastic resin materials used as the lens casting dies 44, 46 may include, for example, polypropylene, polyethylene, polyethylene terephthalate, polystyrene, polycarbonate, vinyl chloride, nylon, polyacetal, fluororesins, and the like.

The female mold molding die 40 includes a first die 50 furnished in its center section with a resin mold molding face 48 of concave shape, and a second die 54 furnished in its center section with a resin mold molding face 52 of convex shape. In particular, the convex resin mold molding face 52 of the second die 54 has in its center section contours that correspond to the lens back face 18 and the outside peripheral face 32 of the edge portion 30 of the intraocular lens 10.

Here, on the resin mold molding face 52 of the second die 54 there is formed a periodic pattern transfer face 55 having a periodic pattern of a multitude of minute linear grooves and lands, situated at a location corresponding to the back face peripheral portion 26 and the outside peripheral face 32 of the edge portion 30 of the intraocular lens 10. No particular limitation is imposed as to the specific method for producing the periodic pattern transfer face 55, and it would be acceptable for example to employ a cutting process using a cutting bite or the like; however, in preferred practice, lithography or a mode that involves machining under non-contact conditions by exposing the resin mold molding face 52 to radiation or a laser beam is employed. It is particularly preferred to employ a mode wherein the resin mold molding face 52 is bombarded at output close to the machining threshold, by a laser pulse of extremely short pulse width such as femtosecond or picosecond laser pulses having pulse width of between $1\times10^{-16}$ second and $1\times10^{-7}$ second, preferably between $1\times10^{-15}$ second and $1\times10^{-9}$ second, to give rise to ablation on the resin mold molding face 52 and produce a periodic pattern.

For the laser beam in the present embodiment, with the laser output at the machining threshold, femtosecond laser pulses with wavelength of 800 nm, pulse width of 180 fs, and repetition frequency of 1 KHz are directed onto a location corresponding to the back face peripheral portion 26 on the resin mold molding face 52 of the second die 54, in a direction corresponding to the lens diametrical direction, and onto a location corresponding to the outside peripheral face 32 of the edge portion 30, in a direction corresponding to the lens thickness direction. A periodic pattern of micro grooves and lands formed parallel to the direction of electrical field oscillation direction of the polarized laser beam is produced at locations corresponding to the back face peripheral portion 26 and to the outside peripheral face 32 of the edge portion 30 on the resin mold molding face 52. The second die 54 is then rotated relative to the laser beam about the lens geometric axis on the resin mold molding face 52. This results in formation of a periodic pattern transfer face 55 having minute linear grooves and lands extending for prescribed lengths in the lens circumferential direction, at locations corresponding to the back face peripheral portion 26 and to the outside peripheral face 32 of the edge portion 30 on the resin mold molding face 52. Specifically, the direction of extension of the groove portions and land portions is aligned with the lens circumferential direction, and the periodic pattern produced by these groove portions and land portions is formed in the lens diametrical direction at the location corresponding to the back face peripheral portion 26, and in the lens thickness direction at the location corresponding to the outside peripheral face 32 of the edge portion 30.

The first die 50 and the second die 54 are then closed in the axial direction by a mold closing unit, not shown, to define a mold cavity 56 between the mated faces of the two dies 50, 54. The mold cavity 56 is filled with thermoplastic resin material injected for example by an injection unit (not shown) into the mold cavity 56 through a sprue or runner 58 and cooled to solidity to mold the lens casting female die 44. By virtue of being formed by the resin mold molding face 52 of the second die 54 in this way, a lens molding face 60 of the lens casting female die 44 is given contours corresponding to the back face of the intraocular lens 10 including the lens back face 18, and to the outside peripheral face of the intraocular lens 10 including the outside peripheral face 32 of the edge portion 30. Then, during resin molding of the lens casting female die 44 using the female mold molding die 40, the periodic pattern of the periodic pattern transfer face 55 which has been formed on the resin mold molding face 52 of the female mold molding die 40 becomes transferred to the lens molding face 60 of the lens casting female die 44. As a result, a periodic pattern molding face 61 having a multitude of minute linear grooves and lands formed therein is formed on the lens molding face 60 of the female mold molding die 40, in sections thereof corresponding to the locations for producing the objective back face peripheral portion 26 and the outside peripheral face 32 of the edge portion 30 on the intraocular lens 10.

The male mold molding die 42 meanwhile includes a first die 64 furnished in its center section with a resin mold molding face 62 of concave shape, and a second die 68 furnished in its center section with a resin mold molding face 66 of convex shape. In particular, the concave resin mold molding face 62 of the first die 64 has in its center section contours that correspond to the lens front face 16 of the intraocular lens 10.

The first and second dies 64, 68 are then closed in the axial direction by a mold closing unit, not shown, to define a mold cavity 72 between the mated faces of the two dies 64, 68. This mold cavity 72 is filled with thermoplastic resin material injected through a runner 58 and cooled to solidity, and the molded article made of the resin material is then removed by parting the two dies 64, 68. The lens casting male die 46 is obtained in this manner. By virtue of being formed by the resin mold molding face 62 of the first die 64 in this way, a lens molding face 74 of the lens casting male die 46 is given contours corresponding to the front face of the intraocular lens 10 including the lens front face 16.

Next, the objective intraocular lens 10 is mold cast using the lens casting female die 44 with the periodic pattern molding face 61 formed thereon, and the lens casting male die 46.

First, the lens casting female die 44 is supported so as to open vertically upward, and a polymerizable monomer 78 like any of those mentioned above for use as the intraocular lens 10 material is placed in the saucer-like region formed by the concave lens molding face 60.

Figure 6:
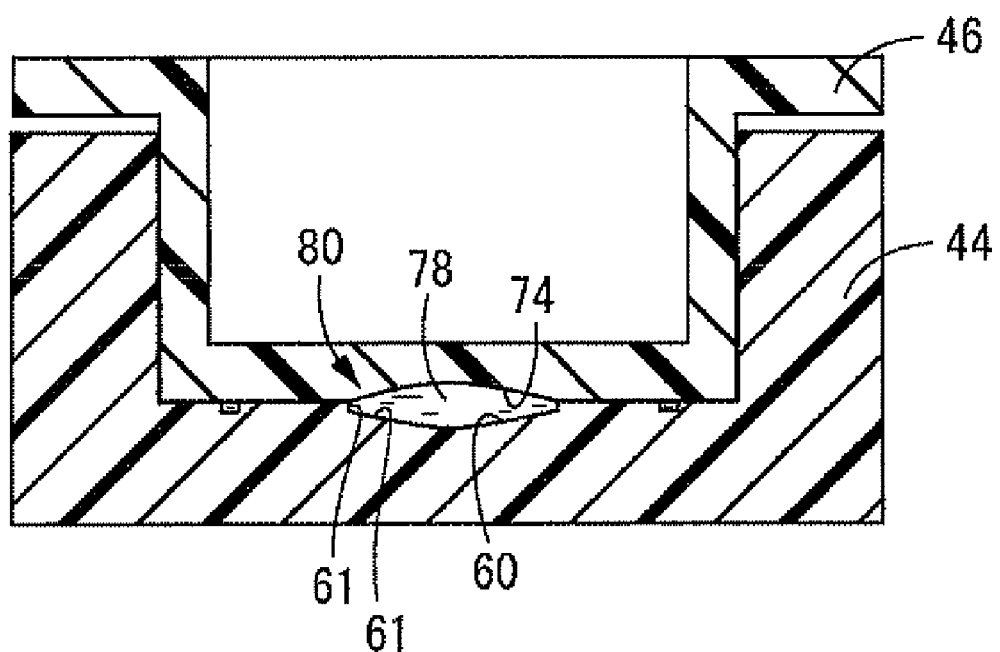
FIG. 6 is a longitudinal sectional specific view depicting a resin mold for use in production of the intraocular lens of FIG. 1.

Next, as shown in FIG. 6, the lens casting male die 46 is juxtaposed against the lens casting female die 44 from above in the axial direction (the vertical direction in FIG. 6) and mated fitting together with it, forming a sealed mold cavity 80 filled with the polymerizable monomer 78. Then, with the two dies 44, 46 held in mated condition, a process to polymerize the polymerizable monomer 78 is carried out. The polymerization process may involve photopolymerization or thermal polymerization, depending on the polymerizable monomer 78 which is being used.

After polymerizing the polymerizable monomer 78, the lens casting female die 44 and the lens casting male die 46 are parted, and the intraocular lens consisting of the polymerized mold-cast article is extracted from the mold to obtain the objective intraocular lens 10. Through this process, the minute linear grooves and lands of the periodic pattern molding face 61 formed on the lens molding face 60 of the lens casting female die 44 are transferred to the back face peripheral portion 26 of the lens back face 18 and the outside peripheral face 32 of the edge portion 30 in the intraocular lens 10 to create the cell inducing regions in the back face peripheral portion 26 and the outside peripheral face 32 of the edge portion 30.

According to this manufacturing method, a periodic pattern of minute linear grooves and lands formed on the female mold molding die 40 is transferred to the intraocular lens 10 through the agency of the lens casting female die 44, thereby minimizing deviation in contours among the minute linear grooves and lands of different lenses when large numbers of intraocular lenses are manufactured. Moreover, once the periodic pattern transfer face 55 has been created on the female mold molding die 40, subsequent manufacture may take place through steps comparable to those of a conventional mold casting method. Accordingly, there is substantially no increase in the number of steps on the intraocular lens production line, and intraocular lenses 10 having minute linear grooves and lands may be obtained with outstanding efficiency.

Further, according to the present manufacturing method, the periodic pattern transfer face 55 is produced on the lens casting female die 44 by a non-contact process involving ablation with femtosecond laser pulses. Since there is substantially no heating up of the machining surface, heat induced deformation is negligible, and periodic patterns of minute linear grooves and lands may be formed reproducibly and with high precision.

In the present manufacturing method, it is also possible to employ radiation in place of a laser beam for producing the periodic pattern transfer face 55 on the lens casting female die 44; an electron beam or the like may be appropriately employed as the radiation for this purpose. Through proper adjustment of the bombardment energy, machining may be carried out with the electron beam, without heating of the machining surface.

While the present invention has been described in detail in terms of a preferred embodiment, this is merely exemplary and it is to be understood that the invention is by no means limited to the details of the illustrated embodiment and may be embodied with various changes, modifications and improvements which may occur to those skilled in the art, and insofar as such modes do not depart from the spirit of the invention they are considered to fall within the scope of the invention.

For example, the cell inducing regions may be formed on any lens surface selected from the lens front face, the lens back face, and the outside peripheral face of the edge portion; or formed over all of these lens surfaces. In the preceding embodiment, it would be possible to form microgrooves 28 on the front face peripheral portion 24 in addition to the back face peripheral portion 26 to create the cell inducing regions, or to create cell inducing regions in the front and back face center portions 20, 22 as well; it is also possible to create a cell inducing region on the outside peripheral face 32 of the edge portion 30 only.

Cell inducing regions according to the present invention may be employed in combination with sharp edge contours taught in the prior art, such as those disclosed in JP-A 2005-507742 and WO2004/096099 for example.

In the manufacturing method described previously, it is possible for the resin mold, i.e. the lens casting female die 44, to undergo laser processing to produce the periodic pattern molding face 61, rather than subjecting the die, i.e. the female mold molding die 40, to laser processing. Alternatively, the intraocular lens may be formed directly from a die without relying on a resin mold. In this case, contours that are the reverse of the minute linear grooves and lands formed on a die would be transferred to the lens surfaces to produce the cell inducing regions. Or, the minute linear grooves and lands may be produced by directly bombarding with a laser beam or radiation the lens surface of a lens molded article manufactured by a conventional known manufacturing method, such as cutting from lens blanks for example.

EXAMPLES

Tests carried out for the purpose of demonstrating the technological advantages afforded by the intraocular lens and manufacturing method in accordance with the present invention are presented below as Examples. Naturally, the disclosure in these Examples should not be construed as limiting the present invention in any way.

Plates corresponding to the intraocular lens according to the present invention, endowed with periodic patterns according to the manufacturing method of the present invention (periodic machined plates) and plates corresponding to intraocular lenses of conventional design lacking periodic patterns (non-periodic machined plates) were prepared and were subjected to comparative tests regarding the direction of cell growth in the respective plates.

Figure 7:
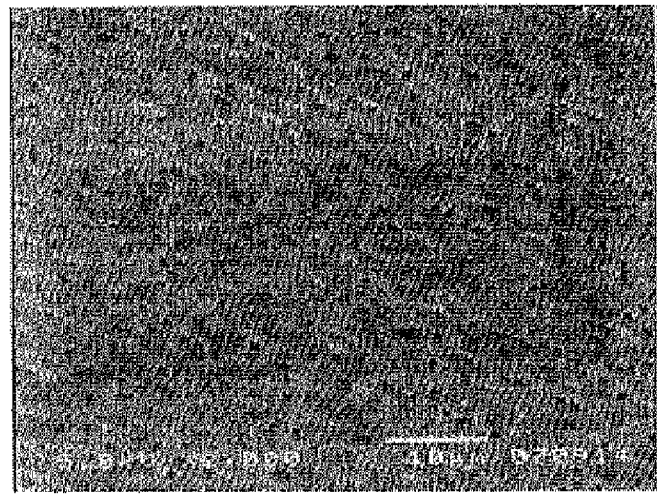
FIG. 7 shows an observed image of a surface of a microperiodic pattern formation zone on a plate die.
Figure 8:
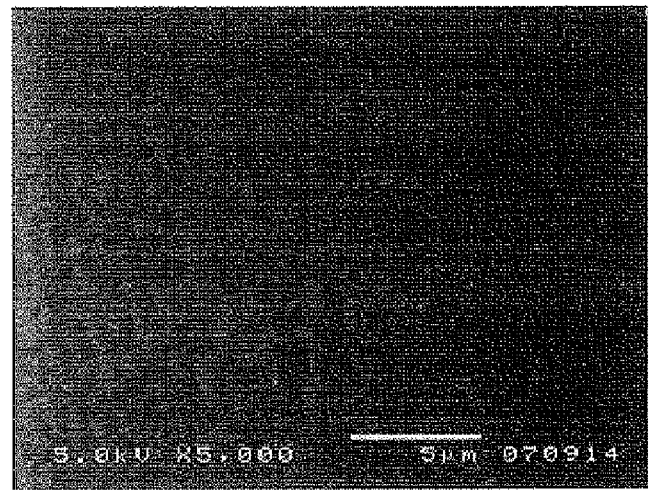
FIG. 8 shows an observed image of a surface of a microperiodic pattern non-formation zone on the plate die.

To produce the periodic machined plates, a plate die of mechanical construction grade carbon steel material (S45C) was prepared, and a femtosecond laser shaped to a line by a cylindrical lens was directed onto the surface of the plate die while oriented with the polarization direction parallel to the lens diametrical direction, and bombardment was carried out parallel to the lens diametrical direction with the output at the machining threshold. The plate die was then rotated to produce a circular microperiodic pattern on the plate die. The femtosecond laser had 800 nm wavelength, pulse width of 180 fs, and repetition frequency of 1 kHz. The femtosecond laser machining unit was a femtosecond surface modification unit (trade name Surfbeat R) made by Canon Machinery Corp. and equipped with a femtosecond laser light source (trade name IFRIT) made by Cyber Laser Inc. as the light source. FIG. 7 depicts the surface of a microperiodic pattern formation zone on a plate die, and FIG. 8 depicts the surface of microperiodic pattern non-formation zone on the plate die.

Next, using the plate die with the microperiodic pattern formed in the above manner, a nylon resin mold was produced by injection molding, transferring the microperiodic pattern on the plate die surface to the resin mold. The resin mold having the transferred microperiodic pattern was then used to polymerization cast mold an acrylate material to obtain cyclic pattern plates 11 mm in diameter and 1 mm in thickness, as an Example.

Meanwhile, as a Comparative Example, non-periodic machined plates were prepared by a method similar to the above, but without subjecting the die plate to laser machining.

The periodic machined plates and non-periodic machined plates underwent testing by the following procedure.

1. Once cells (V79 cells: Chinese hamster lung derived fibroblasts, JCRB0603) on a flask culture surface were observed to have reached 60% to 80% confluence, they were washed with PBS (−). The cells were then detached with trypsin solution, and a culture broth (MEM medium containing 10 vol % bovine calf serum (MEM10 medium)) was added to prepare a cell suspension. The cell suspension was added to a mixture of trypan blue solution and PBS (−), and the number of cells was counted using a counting chamber. The solution was further diluted with culture broth to prepare a cell suspension containing approximately $5 \times 10^3$ cells/mL.

2. The periodic machined plates and non-periodic machined plates were respectively arranged on the bottom faces of wells, and after aliquoting 0.5 mL portions of culture broth into the respective wells, the cell suspension prepared according to step 1 above was seeded in 0.1 mL portions in order to seed approximately 500 cells per well, which were then cultured in a carbon dioxide culture apparatus.

3. Three days after seeding the cells were fixed with formalin, and once fixed were washed several times with distilled water, and air dried naturally.

4. The periodic machined plates and non-periodic machined plates prepared in steps 1 to 3 were examined under a differential interference microscope.

Figure 9:
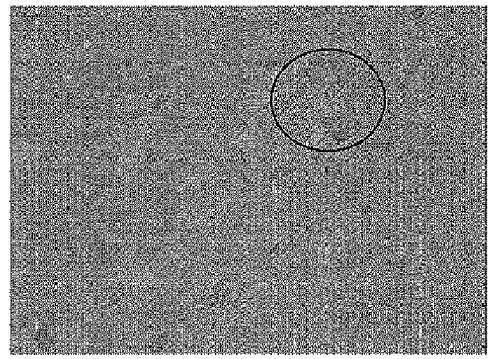
FIG. 9 shows an observed image of a surface of a periodic machined plate.
Figure 10:
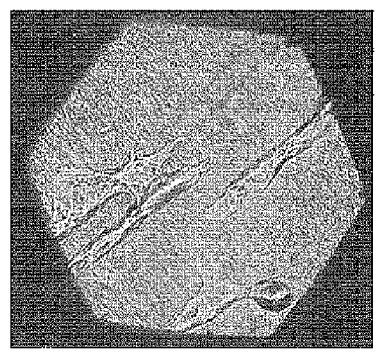
FIG. 10 shows an enlarged observed image of FIG. 9.
Figure 11:
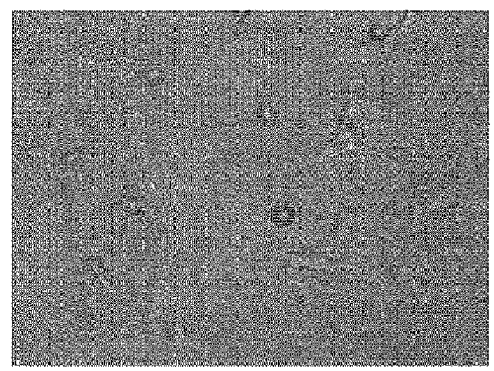
FIG. 11 shows an observed image of a surface of a non-periodic machined plate.

FIGS. 9 and 10 show a periodic machined plate surface and an enlarged image thereof, and FIG. 11 shows a non-periodic machined plate surface. The arrows in FIGS. 9 and 10 indicate the extension direction of the grooves forming the periodic pattern, which corresponds to the lens circumferential direction. FIG. 10 is an enlargement of the circled area in FIG. 9. As will be appreciated from these test results, it was observed that on the non-periodic machined plate lacking a periodic pattern, the directions of the fusiform long axes of the growing cells were oriented irregularly, whereas on the periodic machined plate having a periodic pattern, the directions of the fusiform long axes of the growing cells were generally oriented in the groove extension direction. This demonstrated that according to the intraocular lens of present invention, the cell growth direction may be induced towards the groove extension direction, i.e. the lens circumferential direction.

Next, a plate corresponding to the intraocular lens of the present invention (periodic machined plate) and a plate corresponding to an intraocular lens of conventional design (non-periodic machined plate) were prepared, and the plates were measured for visible light transmittance.

The periodic machined plate and the non-periodic machined plate were obtained by a method comparable to the manufacturing method described previously, except for using nickel plated STAVAK™ for the plate dies and silicon-impregnated hydrated material as the plate material.

Figure 12:
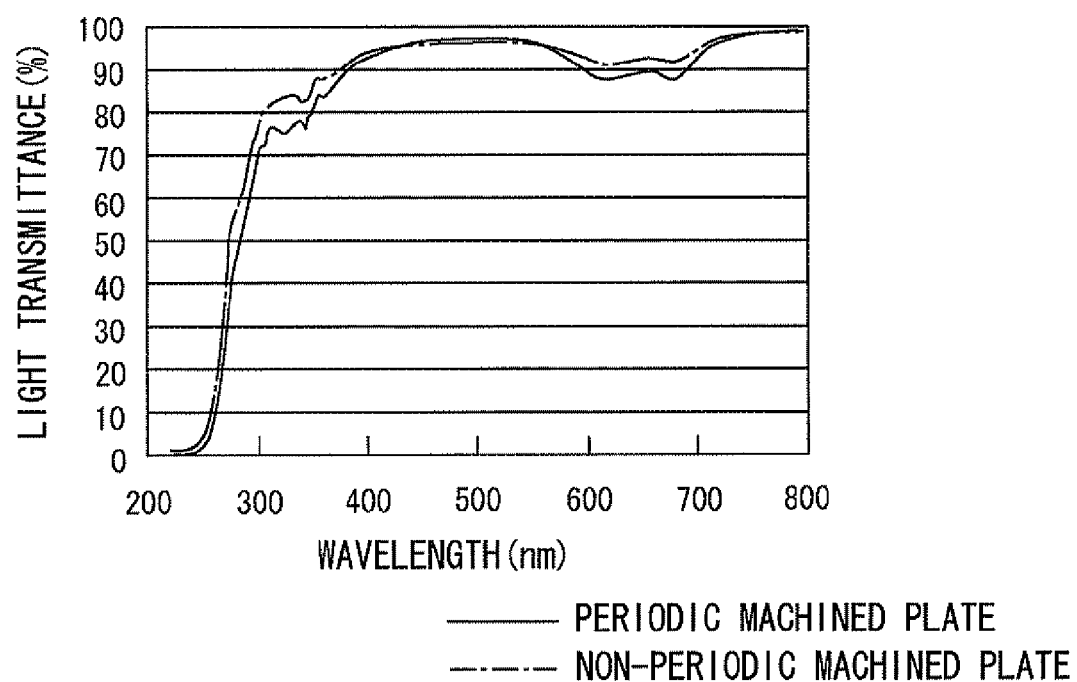
FIG. 12 is a graph showing measurements of light transmittance of the periodic machined plate and the non-periodic machined plate.

FIG. 12 shows measurements of light transmittance of the periodic machined plate and the non-periodic machined plate. Light transmittance was measured using a UV/visible light spectrophotometer made by Shimadzu Corp. (trade name: UV-3150).

As will be apparent from FIG. 12, the periodic machined plate corresponding to the intraocular lens according to the present invention exhibited high transmittance of 80% or above in the visible light region between 350 nm and 800 nm. Compared with the non-periodic machined plate corresponding to an intraocular lens of conventional design, there were substantially no differences between 400 nm and 550 nm or at 700 nm and above, and in other regions the decline was at most about 5%, so transmittance was about the same as with the conventional design. It was demonstrated thereby that the intraocular lens according to the present invention affords effective inhibition of secondary cataracts, while having optical properties substantially identical to conventional designs.

The invention claimed is:

1. An intraocular lens adapted for deployment within a lens capsule, wherein the improvement comprises:
    at least part of a lens surface constituting a cell inducing region in which are directly formed a multitude of microgrooves;
    the microgrooves taking a form of minute linear grooves and lands of depth dimension between 0.01 and 1.0 µm and width dimension between 0.1 and 2.0 µm extending with prescribed length in a circumferential direction on the lens surface; and
    the minute linear grooves and lands being formed with a chained pattern connected in the circumferential direction of the lens surface, and a plurality of the minute linear grooves and lands being formed with a juxtaposed arrangement in a direction orthogonal to the circumferential direction of the lens surface so that the minute linear grooves and lands are formed without intervening spaces throughout the entire cell inducing region and impart visible light transmittance of 60% or above to the cell inducing region.

2. The intraocular lens according to claim 1, wherein the minute linear grooves and lands have circumferential length dimensions of between 1.0 and 50.0 µm.

3. The intraocular lens according to claim 1, wherein the cell inducing region is formed in an outside peripheral section of at least one of a lens front face and a lens back face.

4. The intraocular lens according to claim 3, wherein the cell inducing region is formed on at least one of the lens front face and the lens back face, exclusively in the outside peripheral section thereof which excludes a center section.

5. The intraocular lens according to claim 4, wherein the cell inducing region that is formed exclusively in the outside peripheral section of at least one of the lens front face and the lens back face is a region extending 2 mm or less in a lens diametrical direction from a lens outside edge.

6. The intraocular lens according to claim 1, wherein the minute linear grooves and lands are formed on a surface of an edge portion which includes a lens outside edge face, and the cell inducing region includes the surface of the edge portion.

7. The intraocular lens according to claim 1, wherein in a cross section of the cell inducing region taken in a direction orthogonal to a lens circumferential direction, the minute linear grooves and lands are formed with periodic cross sectional contours represented by a periodic function.

8. The intraocular lens according to claim 1, wherein at least one of the lens surfaces is formed using a resin mold molded by a die having minute linear grooves and lands formed on a molding face thereof so that the minute linear grooves and lands are transferred therefrom; and the cell inducing region is formed through transfer of the minute linear grooves and lands on the resin mold to the lens surface.

9. A method of manufacturing an intraocular lens adapted for deployment within a lens capsule comprising the steps of:
    forming at least one of lens surfaces using a resin mold molded by a die;
    subjecting a resin mold molding face of the die to bombardment with at least one of radiation and a laser beam to produce microgrooves thereon;
    transfer molding the microgrooves produced on the die to a lens molding face of the resin mold; and
    retransferring the microgrooves that were transferred to the resin mold at least one of the lens surfaces to form on at least a portion of the lens surface a cell inducing region having a multitude of microgrooves directly formed therein,
    wherein the microgrooves take the form of minute linear grooves and lands of depth dimension between 0.01 and 1.0 µm and width dimension between 0.1 and 2.0 µm extending with prescribed length in a circumferential direction on the lens surface, and the minute linear grooves and lands are formed with a chained pattern connected in the circumferential direction of the lens surface, and a plurality of the minute linear grooves and lands are formed with a juxtaposed arrangement in a direction orthogonal to the circumferential direction of the lens surface, thereby forming the minute linear grooves and lands without intervening spaces throughout the entire cell inducing region and imparting visible light transmittance of 60% or above to the cell inducing region.

10. The intraocular lens according to claim 1, wherein the plurality of minute linear grooves and lands are formed so as to conjoin with their ends connected to one another, with substantially no space between them in the circumferential direction.

11. The method of manufacturing an intraocular lens according to claim 9, wherein the laser beam is a laser beam having a pulse width of between $1 \times 10^{-16}$ second and $1 \times 10^{-7}$ second.

12. The method of manufacturing an intraocular lens according to claim 9, wherein the plurality of minute linear grooves and lands are formed so as to conjoin with their ends connected to one another, with substantially no space between them in the circumferential direction.

* * * * *